US012577603B2

(12) United States Patent
Ouyang et al.

(10) Patent No.: US 12,577,603 B2
(45) Date of Patent: Mar. 17, 2026

(54) NAD(P)-DEPENDENT RESPONSIVE ENZYMES, ELECTRODES AND SENSORS, AND METHODS FOR MAKING AND USING THE SAME

(71) Applicant: ABBOTT DIABETES CARE INC., Alameda, CA (US)

(72) Inventors: Tianmei Ouyang, Fremont, CA (US); Benjamin J. Feldman, Berkeley, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 17/818,143

(22) Filed: Aug. 8, 2022

(65) Prior Publication Data

US 2022/0395202 A1 Dec. 15, 2022

Related U.S. Application Data

(63) Continuation of application No. 17/403,258, filed on Aug. 16, 2021, now Pat. No. 12,385,077, which is a
(Continued)

(51) Int. Cl.
*C12Q 1/00* (2006.01)
*A61B 5/1486* (2006.01)
(Continued)

(52) U.S. Cl.
CPC .......... *C12Q 1/001* (2013.01); *A61B 5/14865* (2013.01); *C12N 11/082* (2020.01);
(Continued)

(58) Field of Classification Search
CPC ... A61B 5/14865; A61B 5/15; A61B 5/14532; A61B 5/05; A61B 5/1486; C12Q 1/001;
(Continued)

(56) References Cited

U.S. PATENT DOCUMENTS 4,321,123 A 3/1982 Nakamura et al.
4,721,677 A 1/1988 Clark, Jr.
(Continued)

FOREIGN PATENT DOCUMENTS

CN 1735375 A 2/2006
CN 101360450 A 2/2009
(Continued)

OTHER PUBLICATIONS

English Machine Translation of JP2014160024 (Year: 2014).*
(Continued)

*Primary Examiner* — Gurpreet Kaur
(74) *Attorney, Agent, or Firm* — Sterne, Kessler, Goldstein & Fox P.L.L.C.

(57) ABSTRACT

NADP-dependent oxidoreductase compositions, and electrodes, sensors and systems that include the same. Analyte sensors include an electrode having a sensing layer disposed thereon, the sensing layer comprising a polymer and an enzyme composition distributed therein. The enzyme composition includes nicotinamide adenine dinucleotide phosphate ($NAD(P)^+$) or derivative thereof; an $NAD(P)^+$-dependent dehydrogenase; an NAD(P)H oxidoreductase; and an electron transfer agent comprising a transition metal complex.

37 Claims, 3 Drawing Sheets

Related U.S. Application Data continuation of application No. 16/081,162, filed as application No. PCT/US2017/020495 on Mar. 2, 2017, now Pat. No. 11,091,788.

(60) Provisional application No. 62/303,626, filed on Mar. 4, 2016.

(51) Int. Cl.

| | |
|---|---|
| ***C12N 11/082*** | (2020.01) |
| ***C12Q 1/26*** | (2006.01) |
| ***G01N 27/27*** | (2006.01) |
| ***G01N 27/327*** | (2006.01) |
| ***G01N 33/573*** | (2006.01) |
| ***G01N 33/66*** | (2006.01) |

(52) U.S. Cl.

CPC ............. *C12Q 1/004* (2013.01); *C12Q 1/005* (2013.01); *C12Q 1/006* (2013.01); *C12Q 1/26* (2013.01); *G01N 27/3275* (2013.01); *G01N 33/5735* (2013.01); *G01N 33/66* (2013.01); *C12Y 106/05002* (2013.01); *G01N 27/27* (2013.01)

(58) Field of Classification Search

CPC ........ C12Q 1/004; C12Q 1/005; C12Q 1/006; C12Q 1/26; G01N 27/48; G01N 27/26; G01N 27/327; G01N 27/10; G01N 27/06; G01N 27/27; G01N 33/5735; G01N 33/66; C12N 11/082

See application file for complete search history.

(56) References Cited

U.S. PATENT DOCUMENTS

| | | | | | |
|---|---|---|---|---|---|
| 5,262,035 | A | | 11/1993 | Gregg et al. | |
| 5,264,105 | A | | 11/1993 | Gregg et al. | |
| 5,322,063 | A | | 6/1994 | Allen et al. | |
| 5,356,786 | A | | 10/1994 | Heller et al. | |
| 5,593,852 | A | | 1/1997 | Heller et al. | |
| 5,696,314 | A | | 12/1997 | McCaffrey et al. | |
| 5,783,056 | A | | 7/1998 | Hampp et al. | |
| 5,792,621 | A | | 8/1998 | Verostko et al. | |
| 5,820,551 | A | | 10/1998 | Hill et al. | |
| 5,965,105 | A | | 10/1999 | Rayalu et al. | |
| 5,965,106 | A | * | 10/1999 | Pomato .............. | A61K 47/6897 424/179.1 |
| 6,071,391 | A | | 6/2000 | Gotoh et al. | |
| 6,121,009 | A | | 9/2000 | Heller et al. | |
| 6,134,461 | A | | 10/2000 | Say et al. | |
| 6,175,752 | B1 | | 1/2001 | Say et al. | |
| 6,241,863 | B1 | | 6/2001 | Monbouquette | |
| 6,284,478 | B1 | | 9/2001 | Heller et al. | |
| 6,377,894 | B1 | | 4/2002 | Deweese et al. | |
| 6,503,381 | B1 | | 1/2003 | Gotoh et al. | |
| 6,514,460 | B1 | | 2/2003 | Fendrock | |
| 6,514,718 | B2 | | 2/2003 | Heller et al. | |
| 6,541,216 | B1 | | 4/2003 | Wilsey et al. | |
| 6,560,471 | B1 | | 5/2003 | Heller et al. | |
| 6,579,690 | B1 | | 6/2003 | Bonnecaze et al. | |
| 6,600,997 | B2 | | 7/2003 | Deweese et al. | |
| 6,605,200 | B1 | | 8/2003 | Mao et al. | |
| 6,605,201 | B1 | | 8/2003 | Mao | |
| 6,654,625 | B1 | | 11/2003 | Say et al. | |
| 6,676,816 | B2 | | 1/2004 | Mao et al. | |
| 6,736,957 | B1 | | 5/2004 | Forrow et al. | |
| 6,746,582 | B2 | | 6/2004 | Heller et al. | |
| 6,881,551 | B2 | | 4/2005 | Heller et al. | |
| 6,932,894 | B2 | | 8/2005 | Mao et al. | |
| 6,946,299 | B2 | | 9/2005 | Neel et al. | |
| 7,090,756 | B2 | | 8/2006 | Mao et al. | |
| 7,299,082 | B2 | | 11/2007 | Feldman et al. | |
| 7,501,053 | B2 | | 3/2009 | Karinka et al. | |
| 7,520,970 | B2 | | 4/2009 | Sato et al. | |
| 7,563,588 | B2 | | 7/2009 | Gao et al. | |
| 7,754,093 | B2 | | 7/2010 | Forrow et al. | |
| 7,811,231 | B2 | | 10/2010 | Jin et al. | |
| 7,822,557 | B2 | | 10/2010 | Chen et al. | |
| 8,106,780 | B2 | | 1/2012 | Goodnow et al. | |
| 8,268,143 | B2 | | 9/2012 | Liu et al. | |
| 8,435,682 | B2 | | 5/2013 | Heller | |
| 8,444,834 | B2 | | 5/2013 | Liu et al. | |
| 8,545,693 | B2 | | 10/2013 | McColl et al. | |
| 8,761,857 | B2 | | 6/2014 | Feldman et al. | |
| 8,911,908 | B2 | | 12/2014 | Sakai et al. | |
| 9,290,839 | B2 | | 3/2016 | Wang et al. | |
| 9,775,549 | B2 | | 10/2017 | Ouyang et al. | |
| 9,914,952 | B2 | | 3/2018 | Ouyang et al. | |
| 9,927,386 | B2 | | 3/2018 | Wang et al. | |
| 9,983,161 | B2 | | 5/2018 | Feldman et al. | |
| 10,022,076 | B2 | | 7/2018 | Hoss et al. | |
| 10,136,816 | B2 | | 11/2018 | Bernstein et al. | |
| 10,201,301 | B2 | | 2/2019 | Heller et al. | |
| 10,702,193 | B2 | | 7/2020 | Simpson et al. | |
| 11,091,788 | B2 | | 8/2021 | Ouyang et al. | |
| 2001/0003045 | A1 | | 6/2001 | Davis et al. | |
| 2003/0042137 | A1 | | 3/2003 | Mao et al. | |
| 2003/0050547 | A1 | | 3/2003 | Lebel et al. | |
| 2003/0068666 | A1 | * | 4/2003 | Zweig .................... | C12Q 1/005 435/14 |
| 2003/0100821 | A1 | | 5/2003 | Heller et al. | |
| 2004/0061232 | A1 | | 4/2004 | Shah et al. | |
| 2005/0148832 | A1 | | 7/2005 | Reghabi et al. | |
| 2005/0215871 | A1 | | 9/2005 | Feldman et al. | |
| 2006/0004272 | A1 | | 1/2006 | Shah et al. | |
| 2006/0076236 | A1 | | 4/2006 | Shah et al. | |
| 2006/0257996 | A1 | | 11/2006 | Simpson et al. | |
| 2007/0007132 | A1 | | 1/2007 | Mao et al. | |
| 2007/0027385 | A1 | | 2/2007 | Brister et al. | |
| 2007/0042377 | A1 | | 2/2007 | Gao et al. | |
| 2007/0095661 | A1 | | 5/2007 | Wang et al. | |
| 2007/0131547 | A1 | * | 6/2007 | Nomoto .................. | H01M 8/16 204/403.01 |
| 2007/0213611 | A1 | | 9/2007 | Simpson et al. | |
| 2007/0235331 | A1 | * | 10/2007 | Simpson .................. | A61B 5/00 204/403.01 |
| 2007/0270672 | A1 | | 11/2007 | Hayter | |
| 2008/0179187 | A1 | | 7/2008 | Ouyang et al. | |
| 2008/0319295 | A1 | | 12/2008 | Bernstein et al. | |
| 2009/0166194 | A1 | | 7/2009 | Sato et al. | |
| 2009/0294306 | A1 | | 12/2009 | Feldman et al. | |
| 2010/0185070 | A1 | | 7/2010 | Brister et al. | |
| 2010/0198034 | A1 | | 8/2010 | Thomas et al. | |
| 2010/0213057 | A1 | | 8/2010 | Feldman et al. | |
| 2010/0230285 | A1 | | 9/2010 | Hoss et al. | |
| 2010/0267161 | A1 | | 10/2010 | Wu et al. | |
| 2010/0268043 | A1 | | 10/2010 | Yodfat et al. | |
| 2010/0324392 | A1 | | 12/2010 | Yee et al. | |
| 2010/0326842 | A1 | | 12/2010 | Mazza et al. | |
| 2011/0039165 | A1 | | 2/2011 | Sugiyama et al. | |
| 2011/0046467 | A1 | | 2/2011 | Simpson et al. | |
| 2011/0065008 | A1 | | 3/2011 | Nakagawa et al. | |
| 2011/0120865 | A1 | | 5/2011 | Bommakanti et al. | |
| 2011/0124993 | A1 | | 5/2011 | Bommakanti et al. | |
| 2011/0124994 | A1 | | 5/2011 | Bommakanti et al. | |
| 2011/0126188 | A1 | | 5/2011 | Bernstein et al. | |
| 2011/0213057 | A1 | | 9/2011 | Fenn et al. | |
| 2011/0213225 | A1 | | 9/2011 | Bernstein et al. | |
| 2011/0256024 | A1 | | 10/2011 | Cole et al. | |
| 2011/0257495 | A1 | | 10/2011 | Hoss et al. | |
| 2012/0132525 | A1 | | 5/2012 | Liu et al. | |
| 2012/0138484 | A1 | | 6/2012 | Bommakanti et al. | |
| 2012/0150005 | A1 | | 6/2012 | Hoss et al. | |
| 2012/0157801 | A1 | | 6/2012 | Hoss et al. | |
| 2012/0181189 | A1 | | 7/2012 | Merchant | |
| 2012/0186997 | A1 | | 7/2012 | Li et al. | |
| 2012/0245447 | A1 | | 9/2012 | Karan et al. | |
| 2012/0283537 | A1 | | 11/2012 | Petisce et al. | |
| 2012/0296186 | A1 | | 11/2012 | Ouyang et al. | |
| 2012/0323098 | A1 | | 12/2012 | Moein et al. | |
| 2013/0059212 | A1 | | 3/2013 | Kusumegi et al. | |
| 2013/0116524 | A1 | | 5/2013 | Cole et al. | |

(56) References Cited

U.S. PATENT DOCUMENTS

| | | | | |
|---|---|---|---|---|
| 2013/0131478 | A1 | 5/2013 | Simpson et al. | |
| 2013/0211219 | A1 | 8/2013 | Coppeta et al. | |
| 2013/0231542 | A1 | 9/2013 | Simpson et al. | |
| 2013/0245412 | A1 | 9/2013 | Rong et al. | |
| 2013/0324820 | A1 | 12/2013 | Petillo et al. | |
| 2014/0054171 | A1 | 2/2014 | Feldman et al. | |
| 2014/0127728 | A1 | 5/2014 | Wilsey | |
| 2014/0176338 | A1 | 6/2014 | He et al. | |
| 2014/0262776 | A1 | 9/2014 | Martin et al. | |
| 2014/0262777 | A1 | 9/2014 | Zhao et al. | |
| 2015/0038814 | A1 | 2/2015 | Staib et al. | |
| 2015/0076004 | A1 | 3/2015 | Gerber et al. | |
| 2015/0207796 | A1 | 7/2015 | Love et al. | |
| 2016/0045147 | A1 | 2/2016 | Ouyang et al. | |
| 2016/0319232 | A1 | 11/2016 | Noritomi et al. | |
| 2016/0328991 | A1 | 11/2016 | Simpson et al. | |
| 2016/0345882 | A1 | 12/2016 | Wu et al. | |
| 2016/0354542 | A1 | 12/2016 | Ward et al. | |
| 2016/0355862 | A1* | 12/2016 | Deng ................. | G01N 27/3271 |
| 2017/0156652 | A1 | 6/2017 | Qiang et al. | |
| 2017/0191958 | A1 | 7/2017 | Gerber et al. | |
| 2017/0202491 | A1 | 7/2017 | Heller et al. | |
| 2017/0238851 | A1 | 8/2017 | Duhamel et al. | |
| 2017/0315077 | A1 | 11/2017 | Rao et al. | |
| 2017/0319111 | A1 | 11/2017 | Simpson et al. | |
| 2018/0014766 | A1 | 1/2018 | Ouyang et al. | |
| 2018/0116604 | A1 | 5/2018 | Newberry | |
| 2018/0275088 | A1 | 9/2018 | Huff et al. | |
| 2019/0004005 | A1 | 1/2019 | Oja et al. | |
| 2019/0024130 | A1 | 1/2019 | Ouyang et al. | |
| 2019/0125230 | A1 | 5/2019 | Feldman | |
| 2019/0271658 | A1 | 9/2019 | Haneda et al. | |
| 2019/0274598 | A1 | 9/2019 | Scott et al. | |
| 2019/0320947 | A1 | 10/2019 | Chen et al. | |
| 2020/0069226 | A1 | 3/2020 | Hahn et al. | |
| 2020/0237275 | A1 | 7/2020 | Feldman et al. | |
| 2020/0237276 | A1 | 7/2020 | Oja et al. | |
| 2020/0237277 | A1 | 7/2020 | Ouyang et al. | |
| 2020/0241015 | A1 | 7/2020 | Ouyang et al. | |
| 2021/0137431 | A1 | 5/2021 | Oja et al. | |
| 2022/0056500 | A1 | 2/2022 | Ouyang et al. | |
| 2022/0168727 | A1 | 6/2022 | Baldwa | |
| 2022/0386910 | A1 | 12/2022 | Oja et al. | |
| 2022/0389475 | A1 | 12/2022 | Ouyang et al. | |
| 2022/0396820 | A1 | 12/2022 | Ouyang et al. | |
| 2023/0054564 | A1 | 2/2023 | Ouyang et al. | |
| 2023/0080107 | A1 | 3/2023 | Ouyang et al. | |
| 2023/0118818 | A1 | 4/2023 | Feldman et al. | |
| 2023/0119512 | A1 | 4/2023 | Feldman et al. | |
| 2023/0121101 | A1 | 4/2023 | Feldman et al. | |
| 2023/0121367 | A1 | 4/2023 | Feldman et al. | |
| 2023/0121769 | A1 | 4/2023 | Feldman et al. | |
| 2023/0122702 | A1 | 4/2023 | Feldman et al. | |
| 2023/0123384 | A1 | 4/2023 | Feldman et al. | |
| 2023/0128038 | A1 | 4/2023 | Feldman et al. | |
| 2024/0247297 | A1 | 7/2024 | Ouyang et al. | |
| 2024/0350047 | A1 | 10/2024 | Oja et al. | |
| 2025/0221643 | A1 | 7/2025 | Ouyang et al. | |
| 2025/0261884 | A1 | 8/2025 | Oja et al. | |

FOREIGN PATENT DOCUMENTS

| | | | |
|---|---|---|---|
| CN | 102047101 | A | 5/2011 |
| CN | 101849180 | B | 8/2017 |
| CN | 113164106 | A | 7/2021 |
| EP | 0990706 | A1 | 4/2000 |
| EP | 3394252 | A1 | 10/2018 |
| EP | 3414325 | A1 | 12/2018 |
| EP | 3597765 | A1 | 1/2020 |
| EP | 4084689 | A1 | 11/2022 |
| GB | 2067764 | A | 7/1981 |
| JP | 2001506742 | A | 5/2001 |
| JP | 2002514744 | A | 5/2002 |
| JP | 2007507711 | A | 3/2007 |
| JP | 2007510155 | A | 4/2007 |
| JP | 2007290504 | A | 11/2007 |
| JP | 2010517054 | A | 5/2010 |
| JP | 2010530790 | A | 9/2010 |
| JP | 2011053211 | A | 3/2011 |
| JP | 2011099849 | A | 5/2011 |
| JP | 2011136186 | A | 7/2011 |
| JP | 2013504053 | A | 2/2013 |
| JP | 2014503080 | A | 2/2014 |
| JP | 2014160024 | A * | 9/2014 |
| JP | 2015198960 | A | 11/2015 |
| JP | 2018029983 | A | 3/2018 |
| JP | 2022172249 | A | 11/2022 |
| WO | WO-03056319 | A2 | 7/2003 |
| WO | WO-2005040404 | A1 | 5/2005 |
| WO | WO-2009105337 | A2 | 8/2009 |
| WO | WO-2010027771 | A1 | 3/2010 |
| WO | WO-2010030912 | A1 | 3/2010 |
| WO | WO-2011030093 | A1 | 3/2011 |
| WO | WO-2012100130 | A1 | 7/2012 |
| WO | WO-2015150263 | A1 | 10/2015 |
| WO | WO-2015195352 | A1 | 12/2015 |
| WO | WO-2016025064 | A1 | 2/2016 |
| WO | WO-2016174456 | A1 | 11/2016 |
| WO | WO-2016174458 | A1 | 11/2016 |
| WO | WO-2017151952 | A1 | 9/2017 |
| WO | WO-2018067235 | A1 | 4/2018 |
| WO | WO-2019006413 | A1 | 1/2019 |

OTHER PUBLICATIONS

Supplementary European Search Report in EP Application No. 17760843, Feb. 26, 2020, 2 pages.

International Search Report and Written Opinion of PCT/US2017/020495, mailed Jul. 10, 2017, 23 pages.

Nikitina, O., et al., "Bi-enzyme biosensor based on NAD+-and glutathione-dependent recombinant formaldehyde dehydrogenase and diaphorase for formaldehyde assay," Sensors and Actuators 125(1):1-9, (2007).

Office Action mailed Jul. 22, 2020 in U.S. Appl. No. 16/081,162, 10 pages.

Office Action mailed Dec. 30, 2020 in U.S. Appl. No. 16/081,162, 12 pages.

Nakabayashi, Y., et al., "Evaluation of osmium(II) complexes as electron transfer mediators accessible for amperometric glucose sensors," Anal Sci 17(8):945-950, The Japan Society for Analytical Chemistry, Japan (Aug. 2001).

Notice of Allowance mailed Apr. 13, 2021 in U.S. Appl. No. 16/081,162, 7 pages.

Office Action mailed Jan. 31, 2024, in U.S. Appl. No. 17/819,038, 11 pages.

Office Action mailed Mar. 12, 2024, in U.S. Appl. No. 17/818,770, 14 pages.

Office Action mailed Mar. 25, 2024, in U.S. Appl. No. 17/403,258, 9 pages.

Burmeister, J.J., and Gerhardt, G.A., "Self-referencing Ceramic-based Multisite Microelectrodes for the Detection and Elimination of Interferences from the Measurement of L-glutamate and Other Analytes," Analytical Chemistry, 73(5):1037-1042, American Chemical Society, United States (Mar. 2001).

Cardosi, M., and Liu, Z., "Amperometric Glucose Sensors for Whole Blood Measurement Based on Dehydrogenase Enzymes," Chapter 13 in Dehydrogenases, pp. 319-354, Canuto, R. A., ed., InTechOpen, Croatia, 36 pages (Nov. 2012).

Co-pending Application, U.S. Appl. No. 18/068,860, inventors Feldman, B. J., et al., filed on Dec. 20, 2022, 78 pages.

English Language Translation of JP2014160024A, 2014, 22 Pages.

Final Office Action for U.S. Appl. No. 16/582,583 mailed on Apr. 19, 2023, 18 pages.

Final Office Action for U.S. Appl. No. 16/582,583 mailed on May 16. 2024, 21 pages.

Final Office Action for U.S. Appl. No. 16/774,835 mailed on Apr. 18, 2022, 24 pages.

Final Office Action for U.S. Appl. No. 16/774,835 mailed on Dec. 24, 2024, 25 pages.

(56) References Cited

OTHER PUBLICATIONS

Final Office Action for U.S. Appl. No. 16/774,909 mailed on April 9. 2024, 13 pages.
Final Office Action for U.S. Appl. No. 17/138,477, mailed on Apr. 3, 2024, 12 pages.
Final Office Action for U.S. Appl. No. 17/138,477, mailed on Mar. 17, 2023, 12 pages.
Final Office Action for U.S. Appl. No. 17/403,258, mailed on Nov. 13, 2024, 11 pages.
Final Office Action for U.S. Appl. No. 18/068,019 mailed on Oct. 17, 2024, 17 pages.
Final Office Action for U.S. Appl. No. 18/068,072 mailed on Oct. 18, 2024, 13 pages.
Final Office Action for U.S. Appl. No. 18/068,077 mailed on Jan. 28, 2025, 26 pages.
Final Office Action for U.S. Appl. No. 18/068,704 mailed on Jan. 24, 2025, 16 pages.
Final Office Action for U.S. Appl. No. 18/068,714, mailed on Oct. 18, 2024, 15 pages.
Final Office Action for U.S. Appl. No. 18/068,860 mailed on Oct. 18, 2024, 15 pages.
Final Office Action for U.S. Appl. No. 16/774,835, mailed on Sep. 12, 2023, 16 pages.
Final Office Action for U.S. Appl. No. 16/774,909, mailed on Dec. 21, 2022, 13 pages.
Final Office Action for U.S. Appl. No. 17/818,912, mailed on Oct. 25, 2024, 11 pages.
Final Office Action for U.S. Appl. No. 17/819,038, mailed on Aug. 26, 2024, 10 pages.
Final Office Action mailed Jul. 30, 2024, U.S. Appl. No. 17/818,770, Ouyang, T., et al., filed Aug. 10, 2022, 13 pages.
Guiseppi-Elie, A., et al., "Design of a subcutaneous implantable biochip for monitoring of glucose and lactate," IEEE Sensors Journal 5(3):345-355, Institute of Electrical and Electronics Engineers, United States (Jun. 2005).
International Search Report and Written Opinion for International Application No. PCT/US2019/052942, dated on Nov. 28, 2019, 17 pages.
International Search Report and Written Opinion for International Application No. PCT/US2020/015365, mailed May 28, 2020, 14 pages.
International Search Report and Written Opinion for International Application No. PCT/US2020/015400. mailed on Apr. 9, 2020, 14 pages.
International Search Report and Written Opinion for International Application No. PCT/US2020/015321, mailed on Apr. 9, 2020, 14 pages.
Monteiro, T et al., "Construction of Effective Disposable Biosensors for Point of Care Testing of Nitrite." Talanta 142:246-251, Elsevier, Netherlands (Sep. 2015).
Mueller. S., et al.. The GOX/CAT system: A Novel Enzymatic Method to Independently Control Hydrogen Peroxide and Hypoxia in Cell Culture Advances in Medical Sciences 54(2):121-135, Elsevier, Netherlands (Dec. 2009).
Non-Final Office Action for U.S. Appl. No. 16/582,583, mailed on Oct. 3, 2023, 21 pages.
Non-Final Office Action for U.S. Appl. No. 16/582,583 mailed on Sep. 1, 2022, 20 pages.
Non-Final Office Action for U.S. Appl. No. 16/774,835 mailed on Apr. 15, 2024, 16 pages.
Non-Final Office Action for U.S. Appl. No. 16/774,835 mailed on Sep. 17, 2021, Feldman, B. J., et al., filed Jan. 28, 2020, 21 pages.
Non-Final Office Action for U.S. Appl. No. 16/774,841, mailed on Jun. 24, 2022, 10 pages.
Non-Final Office Action for U.S. Appl. No. 16/774,841, mailed on Nov. 16, 2022, 10 pages.
Non-Final Office Action for U.S. Appl. No. 16/774,909, mailed on Aug. 8, 2023, 14 pages.
Non-Final Office Action for U.S. Appl. No. 16/774,909, mailed on Jun. 2, 2022, 13 pages.
Non-Final Office Action for U.S. Appl. No. 17/138,477. mailed on Aug. 21, 2023, 12 pages.
Non-Final Office Action for U.S. Appl. No. 17/138,477, mailed on Sep. 12, 2022, 10 pages.
Non-Final Office Action for U.S. Appl. No. 17/151,274, mailed on Nov. 25, 2022, 13 pages.
Non-Final Office Action for U.S. Appl. No. 17/151,274, mailed on Sep. 7, 2023, 13 pages.
Non-Final Office Action for U.S. Appl. No. 17/818,770, mailed on Nov. 5, 2024, 14 pages.
Non-Final Office Action for U.S. Appl. No. 17/819,038, mailed on Mar. 20, 2025, 11 pages.
Non-Final Office Action for U.S. Appl. No. 17/819,099 mailed on Mar. 5, 2024. 14 pages.
Non-Final Office Action for U.S. Appl. No. 17/819,099, mailed on Sep. 22, 2023, 24 pages.
Non-Final Office Action for U.S. Appl. No. 18/068,019, dated on Feb. 29, 2024, 12 Pages.
Non-Final Office Action for U.S. Appl. No. 18/068,072 mailed on Feb. 15, 2024, 13 pages.
Non-Final Office Action for U.S. Appl. No. 18/068,077 mailed on Jul. 30, 2024, 14 pages.
Non-Final Office Action for U.S. Appl. No. 18/068,704 mailed on Jun. 18. 2024, 14 pages.
Non-Final Office Action for U.S. Appl. No. 18/068,714, mailed on Mar. 5, 2024, 14 pages.
Non-Final Office Action for U.S. Appl. No. 18/068,807, mailed on Jan. 29, 2025, 25 pages.
Non-Final Office Action for U.S. Appl. No. 18/068,834 mailed on Jan. 31, 2024, 10 pages.
Non-Final Office Action for U.S. Appl. No. 18/068,834 mailed on Oct. 18, 2024, 15 pages.
Non-Final Office Action for U.S. Appl. No. 18/068,860 mailed on Jul. 15, 2024, 13 pages.
Non-Final Office Action for U.S. Appl. No. 16/774,835, mailed on Mar. 2, 2023, 14 pages.
Non-Final Office Action mailed Apr. 26, 2024, in U.S. Appl. No. 17/818,912, Ouyang, T., et al., filed Aug. 10, 2022, 13 pages.
Non-Final Office Action mailed May 7, 2024, in U.S. Appl. No. 17/819,151, Ouyang, T., et al., filed Aug. 11, 2022, 13 pages.
Non-Final Office Action mailed Sep. 16, 2024, in U.S. Appl. No. 18/597,704, Ouyang, T., et al., filed Mar. 6, 2024, 9 pages.
Notice of Allowance for U.S. Appl. No. 16/774,841 mailed on Aug. 16. 2023, 8 pages.
Notice of Allowance for U.S. Appl. No. 16/774,841 mailed on Feb. 9, 2024, 3 pages.
Notice of Allowance for U.S. Appl. No. 16/774,909, dated on Sep. 29, 2024, 10 pages.
Notice of Allowance for U.S. Appl. No. 17/151,274 mailed on Feb. 7, 2024. 8 pages.
Notice of Allowance for U.S. Appl. No. 17/819,099, dated on Jul. 9, 2024, 8 pages.
Notice of Allowance for U.S. Appl. No. 17/819,151, mailed on Oct. 22, 2024, 7 pages.
Pickup, J.C., "Glucose Sensors: Present and Future," International Textbook of Diabetes Mellitus, Third Edition, Defronzo, R.A., eds., 2:1686-1694, John Wiley & Sons Inc., United States (2004), 13 Pages.
Pundir, C.S., et al., "Biosensing Methods for Determination of Creatinine: A Review," Biosensors and Bioelectronics Journal 126:707-724, Elsevier Advanced Technology, United Kingdom (Feb. 2019).
Shi, G., et al., "The Study of Nafion/xanthine Oxidase/au Colloid Chemically Modified Biosensor and Its Application in the Determination of Hypoxanthine in Myocardial Cells in Vivo," The Analyst 127(3):396-400, Royal Society of Chemistry, United Kingdom (Mar. 2002).
Alva, S., et al., "Feasibility of Continuous Ketone Monitoring in Subcutaneous Tissue Using a Ketone Sensor," Journal of Diabetes Science and Technology 15(4):768-774, Sage, United States (Jul. 2021).
Co-pending, U.S. Appl. No. 19/320,168, filed Sep. 5, 2025.
Co-pending, U.S. Appl. No. 19/320,172, filed Sep. 5, 2025.
Co-pending, U.S. Appl. No. 19/320,176, filed Sep. 5, 2025.

(56) References Cited

OTHER PUBLICATIONS

Co-pending, U.S. Appl. No. 19/320,180, filed Sep. 5, 2025.
Co-pending, U.S. Appl. No. 19/321,772, filed Sep. 8, 2025.
Co-pending, U.S. Appl. No. 19/321,781, filed Sep. 8, 2025.
D'Allegro, J., "Soon your car will know when you are having a heart attack and know how to react," Modem Medicine, CNBC, Accessed at https://www.cnbc.com/2017/11/17/cars-will-know-when-youre-having-a-heart-attack-and-how-to-react.html, Accessed on Oct. 10, 2023, (Nov. 17, 2017), 4 Pages.
Del Cano, R., et al., Ketone Bodies Detection: Wearable and Mobile Sensors for Personalized Medicine an Nutrition, Trends in Analytical Chemistry 159:116938, (Feb. 2023), 11 pages.
Zhang, J.Y., et al., "Continuous Ketone Monitoring: A New Paradigm for Physiologic Monitoring," Journal of Diabetes Science and Technology 15(4):775-780, Sage, United States (Jul. 2021).
Co-pending Application, U.S. Appl. No. 19/340,421, filed Sep. 25, 2025, 119 pages.
Co-pending Application, U.S. Appl. No. 19/340,445, filed Sep. 25, 2025, 118 pages.
Co-pending Application, U.S. Appl. No. 19/340,458, filed Sep. 25, 2025, 119 pages.
Franco, J.H., et al., "Product Analysis of Operating an82 Ethanol/O2 Biofuel Cell Shows the Synergy between Enzymes within an Enzymatic Cascade," Journal of The Electrochemical Society 165(9):H575-H579, (2018).
Kowalewska, B., and Kulesza, P.J., "Toward More Efficient Bioelectrocatalytic Oxidation of Ethanol for Amperometric Sensing and Biofuel Cell Technology," Analytical Chemistry 84(21):9564-9571, American Chemical Society, United States (Nov. 2012).
Non-Final Office Action for U.S. Appl. No. 19/320,176 mailed on Dec. 3, 2025, 15 pages.
Non-Final Office Action for U.S. Appl. No. 19/340,421 mailed on Nov. 28, 2025, 19 pages.
Non-Final Office Action for U.S. Appl. No. 19/340,445 mailed on Nov. 28, 2025, 20 pages.
Non-Final Office Action for U.S. Appl. No. 19/340,458 mailed on Nov. 28, 2025, 22 pages.
Non-Final Office Action for U.S. Appl. No. 18/068,704 mailed on Dec. 16, 2025; 49 pages.
Notice of Allowance for U.S. Appl. No. 17/818,143 mailed on Oct. 28, 2025; 7 pages.
Non-Final Office Action for U.S. Appl. No. 19/320,168 mailed on Dec. 15, 2025; 9 pages.
Non-Final Office Action for U.S. Appl. No. 19/320,172 mailed on Dec. 4, 2025; 10 pages.
Non-Final Office Action for U.S. Appl. No. 19/320,180 mailed on Dec. 16, 2025; 17 pages.

* cited by examiner

NAD(P)-DEPENDENT RESPONSIVE ENZYMES, ELECTRODES AND SENSORS, AND METHODS FOR MAKING AND USING THE SAME

INTRODUCTION

The characterization of analytes in biological fluids has become an integral part of medical diagnoses and assessments of overall health and wellness of a patient. Regularly monitoring the concentration of particular analytes in body fluid of a subject is becoming increasingly important where the results may play a prominent role in the treatment protocol of a patient in a variety of disease conditions. A number of systems are available that analyze an analyte in a bodily fluid, such as blood, plasma, serum, interstitial fluid, urine, tears, and saliva. Such systems monitor the level of particular medically relevant analytes, such as, blood sugars, e.g., glucose, cholesterol, ketones, vitamins, proteins, and various metabolites. In response to this growing importance of analyte monitoring, a variety of analyte detection protocols and devices for laboratory, clinical and at-home use have been developed.

Nicotinamide adenine dinucleotide (NAD(P)+) is a coenzyme found in all living cells. There are many biological molecules that are oxidized by NAD(P)+-dependent dehydrogenases. For example, glucose can be oxidized by NAD-dependent glucose dehydrogenase, alcohol can be oxidized by NAD-dependent alcohol dehydrogenase, 3-Hydroxybutyrate can be oxidized by NAD-dependent D-3-Hydroxybutyrate dehydrogenase, etc. Development of improved sensors for measuring analytes that are oxidized by a variety of different enzymes having a high degree of stability and sensitivity is desirable.

SUMMARY

Embodiments of the present disclosure relate to enzyme compositions, electrodes, sensors, methods for fabricating an analyte sensor as well as methods for monitoring an analyte concentration in a subject with the subject sensors. Disclosed herein are enzyme compositions that include one or more of nicotinamide adenine dinucleotide phosphate (NAD(P)+) or derivative thereof, an NAD(P)+-dependent dehydrogenase, an NAD(P)H oxidoreductase and an electron transfer agent having a transition metal complex. In certain embodiments, enzyme compositions include NAD (P)+ or a derivative thereof and an electron transfer agent having a transition metal complex. The subject enzyme compositions may also include a polymer, such as a heterocycle-containing polymer, and a crosslinker for immobilizing the enzyme composition onto a surface (e.g., on the surface of an electrode). Some or all of these components may be unbound or unconnected, or two or more of these components may be bound or connected together. For example, one or more of the nicotinamide adenine dinucleotide phosphate (NAD(P)+) or derivative thereof, NAD (P)+-dependent dehydrogenase, NAD(P)H oxidoreductase and redox mediator are immobilized on the surface by the polymer. In certain instances, one or more of the nicotinamide adenine dinucleotide phosphate (NAD(P)+) or derivative thereof, NAD(P)+-dependent dehydrogenase, NAD (P)H oxidoreductase and redox mediator are covalently bonded to the polymer. In certain embodiments, the NAD (P)+-dependent dehydrogenase is glucose dehydrogenase, alcohol dehydrogenase or D-3-hydroxybutyrate dehydrogenase. In some embodiments, the NAD(P)H oxidoreductase is diaphorase. Also provided are analyte sensors having the subject enzyme compositions disposed proximate to a working electrode for monitoring an analyte level in a subject as well as methods for fabricating an analyte sensor and methods for using the analyte sensors in monitoring an analyte, such as glucose, an alcohol or 13-hydroxybutyrate in a subject.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

DETAILED DESCRIPTION

Figure 1:
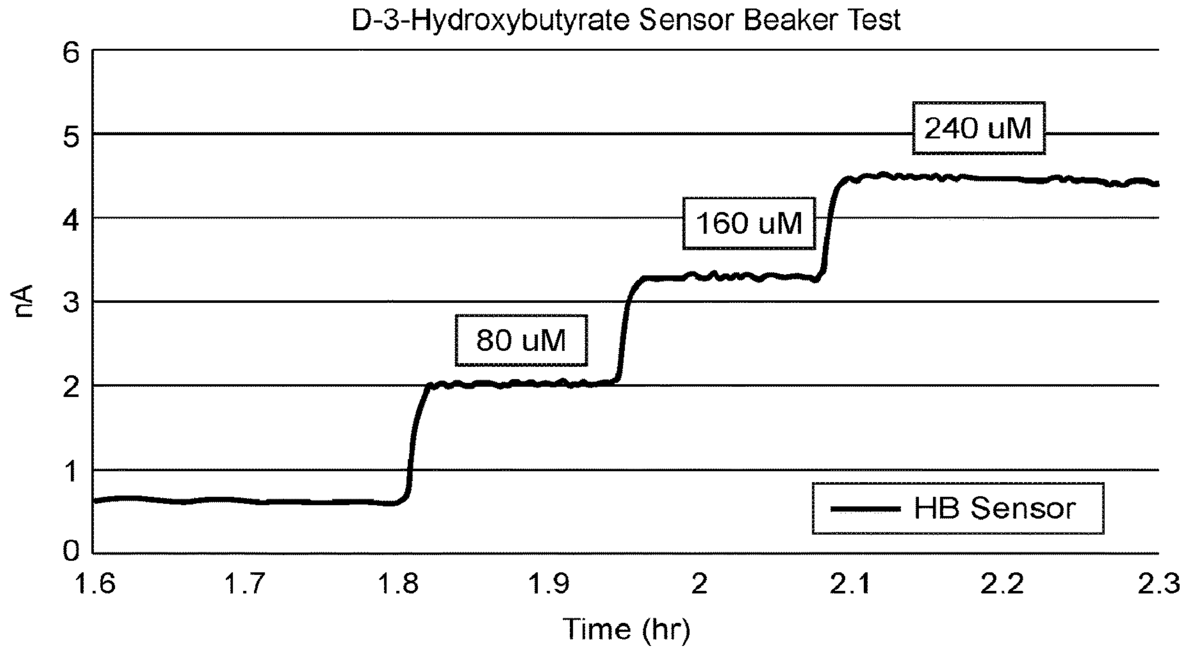
FIG. 1 shows the signal output for a D-3-hydroxybutyrate dehydrogenase sensor over the course of 2.3 hours at varying concentrations of D-3-hydroxybutyrate according to certain embodiments.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be embodied by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "enzymes" encompasses a single enzyme, as well as a combination and/or mixture of two or more different enzymes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular lactates, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

The present disclosure discloses enzyme compositions that include nicotinamide adenine dinucleotide phosphate (NAD(P)+) or derivative thereof and an electron transfer agent having a transition metal complex. In some embodiments, the subject enzyme compositions include nicotinamide adenine dinucleotide phosphate (NAD(P)+) or derivative thereof, an NAD(P)+-dependent dehydrogenase, an NAD(P)H oxidoreductase and an electron transfer agent having a transition metal complex, and analyte sensors with enzyme layers that include immobilized NAD(P)+ or derivative thereof and an electron transfer agent comprising a transition metal complex. Embodiments of the present disclosure relate to enzyme compositions for analyte sensing including where the subject compositions provide for monitoring of an analyte in vivo over an extended period of time. Where the subject enzyme compositions include an NAD(P)+-dependent dehydrogenase, analyte sensors described herein provide for clinically accurate electrochemical measurement of analytes that are catalyzed by an NAD(P)+-dependent dehydrogenase. As described in greater detail below, the subject enzyme compositions provide for clinically accurate electrochemical measurement of analytes as measured by Clark error grid analysis and/or MARD analysis and/or MAD analysis. In particular, the subject enzyme compositions provide for measurement by an analyte sensor incorporating the subject compositions to produce a signal that increases linearly as a function of analyte concentration. In addition, the subject enzyme compositions provide for clinically accurate electrochemical measurement of analytes that are catalyzed by an NAD(P)+-dependent dehydrogenase within 30 seconds of contacting a fluidic sample (e.g., interstitial fluid when the sensor is positioned beneath the surface of a subject's skin) with the sensor. In certain instances, the subject enzyme compositions provide for clinically accurate electrochemical measurements of analytes that are catalyzed by an NAD(P)+-dependent dehydrogenase immediately after contacting the fluidic sample with the sensor.

The subject enzyme compositions include an NAD(P)+-dependent dehydrogenase, such as glucose dehydrogenase, alcohol dehydrogenase or D-3-hydroxybutyrate dehydrogenase. In some embodiments, NAD(P)+-dependent dehydrogenases of interest are oxidoreductases belonging to the enzyme class 1.1.1—

The NAD(P)+-dependent dehydrogenase may be present in the subject compositions in an amount that varies, such as from 0.05 μg to 5 μg, such as from 0.1 μg to 4 μg, such as from 0.2 μg to 3 μg and including from 0.5 μg to 2 μg. As such, the amount of NAD(P)+-dependent dehydrogenase is from 0.01% to 10% by weight of the total enzyme composition, such as from 0.05% to 9.5% by weight, such as from 0.1% to 9% by weight, such as 0.5% to 8.5% by weight, such as from 1% to 8% by weight and including from 2% to 7% by weight of the total enzyme composition.

Enzyme compositions also include nicotinamide adenine dinucleotide phosphate (NAD(P)+) or derivative thereof. In some embodiments, enzyme compositions of interest include nicotinamide adenine dinucleotide phosphate (NAD(P)+). In other embodiments, enzyme compositions include a derivative of nicotinamide adenine dinucleotide phosphate (NAD(P)+). Derivatives of nicotinamide adenine dinucleotide phosphate (NAD(P)+) may include compounds of Formula I:

Formula I

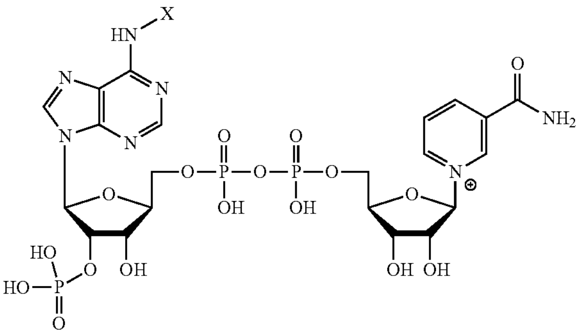

where X is alkyl, substituted alkyl, aryl, substituted aryl, acyl, and aminoacyl.

In some embodiments, X is an aminoacyl substituted alkyl. In some embodiments, X is CH2C(O)NH(CH2)yNH2 where y is an integer from 1 to 10, such as 2 to 9, such as 3 to 8 and including where y is 6. In certain instances, X is CH2C(O)NH(CH2)6NH2. In these embodiments, the derivative of nicotinamide adenine dinucleotide phosphate (NAD(P)+) in the subject enzyme composition is:

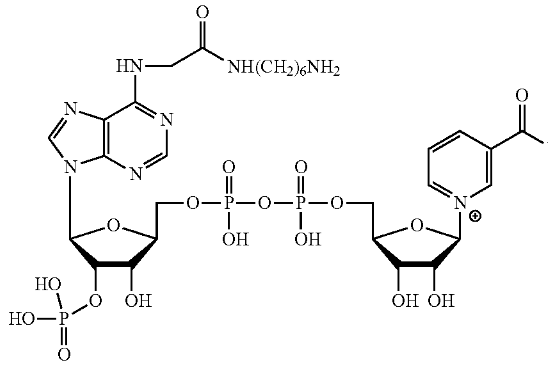

Embodiments of the enzyme composition also include an NAD(P)H oxidoreductase. In certain embodiments, the enzyme composition includes diaphorase The amount of NAD(P)H oxidoreductase (e.g., diaphorase) present in the subject compositions ranges from 0.01 μg to 10 μg, such as from 0.02 μg to 9 μg, such as from 0.03 μg to 8 μg, such as from 0.04 μg to 7 μg, such as from 0.05 μg to 5 μg, such as from 0.1 μg to 4 μg, such as from 0.2 μg to 3 μg and including from 0.5 μg to 2 μg. As such, the amount of NAD(P)H oxidoreductase (e.g., diaphorase) is from 0.01% to 10% by weight of the total enzyme composition, such as from 0.05% to 9.5% by weight, such as from 0.1% to 9% by weight, such as 0.5% to 8.5% by weight, such as from 1% to 8% by weight and including from 2% to 7% by weight of the total enzyme composition.

In some embodiments, the weight ratio of NAD(P)+-dependent dehydrogenase to NAD(P)H oxidoreductase (e.g., diaphorase) ranges from 1 to 10 NAD(P)+-dependent dehydrogenase to NAD(P)H oxidoreductase, such as from 1 to 8, such as from 1 to 5, such as from 1 to 2 and including from 1 to 1 NAD(P)+-dependent dehydrogenase to NAD (P)H oxidoreductase. In other embodiments, the weight ratio of NAD(P)+-dependent dehydrogenase to NAD(P)H oxidoreductase ranges from 10 to 1 NAD(P)+-dependent dehydrogenase to NAD(P)H oxidoreductase, such as from 8 to 1, such as from 5 to 1 and including from 2 to 1 NAD(P)+-dependent dehydrogenase to NAD(P)H oxidoreductase.

Enzyme compositions of interest also include an electron transfer agent having an transition metal complex. They may be electroreducible and electrooxidizable ions or molecules having redox potentials that are a few hundred millivolts above or below the redox potential of the standard calomel electrode (SCE). Examples of transition metal complexes include metallocenes including ferrocene, hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In some embodiments, electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

The subject enzyme compositions may be heterogeneous or homogenous. In some embodiments, each component (i.e., nicotinamide adenine dinucleotide phosphate (NAD (P)+) or derivative thereof, an NAD(P)+-dependent dehydrogenase, an NAD(P)H oxidoreductase and an electron transfer agent having a transition metal complex) is uniformly distributed throughout the composition, e.g., when applied to an electrode, as described in greater detail below. For example, each of nicotinamide adenine dinucleotide phosphate (NAD(P)+) or derivative thereof, an NAD(P)+-dependent dehydrogenase, an NAD(P)H oxidoreductase and an electron transfer agent having a transition metal complex may be distributed uniformly throughout the composition, such that the concentration of each component is the same throughout.

In certain embodiments, the subject enzyme compositions described herein are polymeric. Polymers that may be used may be branched or unbranched and may be homopolymers formed from the polymerization of a single type of monomer or heteropolymers that include two or more different types of monomers. Heteropolymers may be copolymers where the copolymer has alternating monomer subunits, or in some cases, may be block copolymers, which include two or more homopolymer subunits linked by covalent bonds (e.g, diblock or triblock copolymers). In some embodiments, the subject enzyme compositions include a heterocycle-containing polymer. The term heterocycle (also referred to as "heterocycicyl") is used herein in its conventional sense to refer to any cyclic moiety which includes one or more heteroatoms (i.e., atoms other than carbon) and may include, but are not limited to N, P, O, S, Si, etc. Heterocycle-containing polymers may be heteroalkyl, heteroalkanyl, heteroalkenyl and heteroalkynyl as well as heteroaryl or heteroarylalkyl.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, -5-, —S—S—, —O—S—, —NR37R38-, .=N—N=, —N=N—, —N=N—NR39R40, —PR41-, —P(O)2-, —POR42-, —O—P(O)2-, —S—O—, —S—(O)—, —SO2-, —SnR43R44- and the like, where R37, R38, R39, R40, R41, R42, R43 and R44 are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp3 carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

In some embodiments, the heterocycle-containing component is an aromatic ring system. "Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

In certain embodiments, enzyme compositions of interest include a heterocyclic nitrogen containing component, such as polymers of polyvinylpyridine (PVP) and polyvinylimidazole.

The polymeric enzyme compositions may also include one or more crosslinkers (crosslinking agent) such that the polymeric backbone enzyme composition is crosslinked. As described herein, reference to linking two or more different polymers together is intermolecular crosslinking, whereas linking two more portions of the same polymer is intramolecular crosslinking. In embodiments of the present disclosure, crosslinkers may be capable of both intermolecular and intramolecular crosslinkings at the same time.

Suitable crosslinkers may be bifunctional, trifunctional or tetrafunctional, each having straight chain or branched structures. Crosslinkers having branched structures include a multi-arm branching component, such as a 3-arm branching component, a 4-arm branching component, a 5-arm branching component, a 6-arm branching component or a larger number arm branching component, such as having 7 arms or more, such as 8 arms or more, such as 9 arms or more, such as 10 arms or more and including 15 arms or more. In certain instances, the multi-arm branching component is a multi-arm epoxide, such as 3-arm epoxide or a 4-arm epoxide. Where the multi-arm branching component is a multi-arm epoxide, the multi-arm branching component may be a polyethylene glycol (PEG) multi-arm epoxide or a non-polyethylene glycol (non-PEG) multi-arm epoxide. In some embodiments, the multi-arm branching component is a non-PEG multi-arm epoxide. In other embodiments, the multi-arm branching component is a PEG multi-arm epoxide. In certain embodiments, the multi-arm branching component is a 3-arm PEG epoxide or a 4-arm PEG epoxide.

Examples of crosslinkers include but are not limited to polyethylene glycol diglycidyl ether, N,N-diglycidyl-4-glycidyloxyaniline as well as nitrogen-containing multi-functional crosslinkers having the structures:

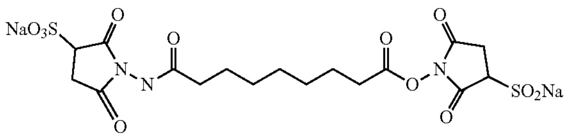

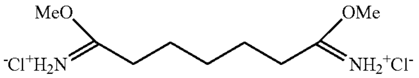

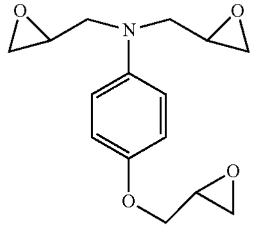

and

-continued

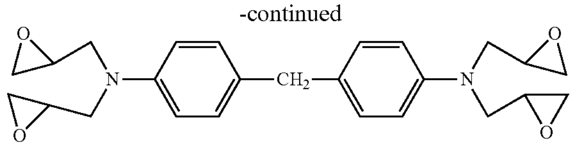

In some instances, one or more bonds with the one or more components of the enzyme composition may be formed such as between one or more of the nicotinamide adenine dinucleotide phosphate (NAD(P)+) or derivative thereof, NAD(P)+-dependent dehydrogenase, NAD(P)H oxidoreductase and electron transfer agent. By bonds is meant any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the enzyme compositions can form cross-links between the polymers of the composition and the NAD(P)+-dependent dehydrogenase, nicotinamide adenine dinucleotide phosphate (NAD(P)+) or derivative thereof, the NAD(P)H oxidoreductase and the electron transfer agent. In certain embodiments, crosslinking of the polymer to the one or more of the NAD(P)+-dependent dehydrogenase, nicotinamide adenine dinucleotide phosphate (NAD(P)+) or derivative thereof, the NAD(P)H oxidoreductase and the electron transfer agent facilitates a reduction in the occurrence of delamination of the enzyme compositions from an electrode.

As described herein, the subject enzyme may be used in an analyte sensor to monitor the concentration of an NAD (P)+-dependent dehydrogenase analyte, such as glucose, an alcohol, a ketone, lactate, or β-hydroxybutyrate, and the sensor may have one or more electrodes with the enzyme composition. In embodiments, the analyte sensor includes: a working electrode having a conductive material the subject enzyme composition proximate to (e.g., disposed on) and in contact with the conductive material. One or more other electrode may be included such as one or more counter electrodes, one or more reference electrodes and/or one or more counter/reference electrodes.

The particular configuration of electrochemical sensors may depend on the use for which the analyte sensor is intended and the conditions under which the analyte sensor will operate. In certain embodiments of the present disclosure, analyte sensors are in vivo wholly positioned analyte sensors or transcutaneously positioned analyte sensors configured for in vivo positioning in a subject. In one example, at least a portion of the sensor may be positioned in the subcutaneous tissue for testing lactate concentrations in interstitial fluid. In another example, at least a portion of the sensor may be positioned in the dermal tissue for testing analyte concentration in dermal fluid.

In embodiments, one or more of the subject enzyme compositions is positioned proximate to (e.g., disposed on) the surface of a working electrode. In some instances, a plurality of enzyme compositions are positioned proximate to the surface of working electrode (e.g., in the form of spots). In certain cases, a discontinuous or continuous perimeter is formed around each of the plurality of enzyme compositions positioned proximate to the surface of the working electrode. Examples of depositing a plurality of reagent compositions to the surface of an electrode as well as forming a discontinuous or continuous perimeter around each reagent composition is described in U.S. Patent Publication No. 2012/0150005 and in U.S. Patent Application No. 62/067,813, the disclosures of which are herein incorporated by reference.

The subject enzyme compositions having nicotinamide adenine dinucleotide phosphate (NAD(P)+) or derivative thereof, NAD(P)+-dependent dehydrogenase, NAD(P)H oxidoreductase and electron transfer agent may be deposited onto the surface of the working electrode as one large application which covers the desired portion of the working electrode or in the form of an array of a plurality of enzyme compositions, e.g., spaced apart from each other. Depending upon use, any or all of the enzyme compositions in the array may be the same or different from one another. For example, an array may include two or more, 5 or more enzyme composition array features containing nicotinamide adenine dinucleotide phosphate (NAD(P)+) or derivative thereof, NAD(P)+-dependent dehydrogenase, NAD(P)H oxidoreductase and electron transfer agent, 10 or more, 25 or more, 50 or more, 100 or more, or even 1000 or more, in an area of 100 $mm^2$ or less, such as 75 $mm^2$ or less, or 50 $mm^2$ or less, for instance 25 $mm^2$ or less, or 10 $mm^2$ or less, or 5 $mm^2$ or less, such as 2 $mm^2$ or less, or 1 $mm^2$ or less, 0.5 $mm^2$ or less, or 0.1 $mm^2$ or less.

The shape of deposited enzyme composition may vary within or between sensors. For example, in certain embodiments, the deposited membrane is circular. In other embodiments, the shape will be of a triangle, square, rectangle, circle, ellipse, or other regular or irregular polygonal shape (e.g., when viewed from above) as well as other two-dimensional shapes such as a circle, half circle or crescent shape. All or a portion of the electrode may be covered by the enzyme composition, such as 5% or more, such as 25% or more, such as 50% or more, such as 75% or more and including 90% or more. In certain instances, the entire electrode surface is covered by the enzyme composition (i.e., 100%).

Fabricating an electrode and/or sensor according to embodiments of the present disclosure produces a reproducible enzyme composition deposited on the surface of the electrode. For example, enzyme compositions provided herein may deviate from each other by 5% or less, such as by 4% or less, such as by 3% or less, such as by 2% or less, such as by 1% or less and including by 0.5% or less. In some embodiments, the sensing composition includes nicotinamide adenine dinucleotide phosphate (NAD(P)+) or derivative thereof and an electron transfer agent. In certain embodiments, deposited enzyme compositions containing nicotinamide adenine dinucleotide phosphate (NAD(P)+) or derivative thereof, NAD(P)+-dependent dehydrogenase, NAD(P)H oxidoreductase and electron transfer agent show no deviation from one another and are identical.

In certain embodiments, methods further include drying the enzyme composition deposited on the electrode. Drying may be performed at room temperature, at an elevated temperature, as desired, such as at a temperature ranging from 25° C. to 100° C., such as from 30° C. to 80° C. and including from 40° C. to 60° C.

Examples of configurations for the subject analyte sensors and methods for fabricating them may include, but are not limited to, those described in U.S. Pat. Nos. 6,175,752, 6,134,461, 6,579,690, 6,605,200, 6,605,201, 6,654,625, 6,746,582, 6,932,894, 7,090,756, 5,356,786, 6,560,471, 5,262,035, 6,881,551, 6,121,009, 6,071,391, 6,377,894, 6,600,997, 6,514,460, 5,820,551, 6,736,957, 6,503,381, 6,676,816, 6,514,718, 5,593,852, 6,284,478, 7,299,082, 7,811,231, 7,822,557 8,106,780, and 8,435,682; U.S. Patent Application Publication Nos. 2010/0198034, 2010/0324392, 2010/0326842, 2007/0095661, 2010/0213057, 2011/0120865, 2011/0124994, 2011/0124993, 2010/0213057, 2011/0213225, 2011/0126188, 2011/0256024, 2011/0257495, 2012/0157801, 2012/0245447, 2012/0157801, 2012/0323098, and 20130116524, the disclosures of each of which are incorporated herein by reference in their entirety.

In some embodiments, in vivo sensors may include an insertion tip positionable below the surface of the skin, e.g., penetrating through the skin and into, e.g., the subcutaneous space, in contact with the user's biological fluid such as interstitial fluid. Contact portions of working electrode, a reference electrode and a counter electrode are positioned on the first portion of the sensor situated above the skin surface. A working electrode, a reference electrode and a counter electrode are positioned at the inserted portion of the sensor. Traces may be provided from the electrodes at the tip to a contact configured for connection with sensor electronics.

In certain embodiments, the working electrode and counter electrode of the sensor as well as dielectric material of are layered. For example, the sensor may include a non-conductive material layer, and a first conductive layer such as conductive polymer, carbon, platinum-carbon, gold, etc., disposed on at least a portion of the non-conductive material layer (as described above). The enzyme composition is positioned on one or more surfaces of the working electrode, or may otherwise be directly or indirectly contacted to the working electrode. A first insulation layer, such as a first dielectric layer may disposed or layered on at least a portion of a first conductive layer and a second conductive layer may be positioned or stacked on top of at least a portion of a first insulation layer (or dielectric layer). The second conductive layer may be a reference electrode. A second insulation layer, such as a second dielectric layer may be positioned or layered on at least a portion of the second conductive layer. Further, a third conductive layer may be positioned on at least a portion of the second insulation layer and may be a counter electrode. Finally, a third insulation layer may be disposed or layered on at least a portion of the third conductive layer. In this manner, the sensor may be layered such that at least a portion of each of the conductive layers is separated by a respective insulation layer (for example, a dielectric layer).

In other embodiments, some or all of the electrodes may be provided in a co-planar manner such that two or more electrodes may be positioned on the same plane (e.g., side-by side (e.g., parallel) or angled relative to each other) on the material. For example, co-planar electrodes may include a suitable spacing there between and/or include a dielectric material or insulation material disposed between the conductive layers/electrodes. Furthermore, in certain embodiments one or more of the electrodes may be disposed on opposing sides of the non-conductive material. In such embodiments, electrical contact may be on the same or different sides of the non-conductive material. For example, an electrode may be on a first side and its respective contact may be on a second side, e.g., a trace connecting the electrode and the contact may traverse through the material. A via provides an avenue through which an electrical trace is brought to an opposing side of a sensor.

The subject analyte sensors be configured for monitoring the level of an analyte (e.g., glucose, an alcohol, a ketone, lactate, β-hydroxybutyrate) over a time period which may range from seconds, minutes, hours, days, weeks, to months, or longer.

In certain embodiments, the analyte sensor includes a mass transport limiting layer, e.g., an analyte flux modulating layer, to act as a diffusion-limiting barrier to reduce the rate of mass transport of the analyte, for example, glucose, an alcohol, a ketone, lactate, β-hydroxybutyrate, when the sensor is in use. The mass transport limiting layers limit the flux of an analyte to the electrode in an electrochemical sensor so that the sensor is linearly responsive over a large range of analyte concentrations. Mass transport limiting layers may include polymers and may be biocompatible. A mass transport limiting layer may provide many functions, e.g., biocompatibility and/or interferent-eliminating functions, etc., or functions may be provided by various membrane layers.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

The membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

Suitable mass transport limiting membranes in the subject analyte sensors may include, but are not limited to those described in U.S. Pat. No. 6,932,894, the disclosure of which is herein incorporated by reference. In certain embodiments, the mass transport limiting membrane is a SMART membrane that is temperature independent. Suitable temperature independent membranes may include, but are not limited to those described in U.S. Patent Publication No. 2012/0296186 and U.S. patent application Ser. No. 14/737,082, the disclosures of which are herein incorporated by reference.

Analyte sensors according to certain embodiments may be configured to operate at low oxygen concentration. By low oxygen concentration is meant the concentration of oxygen is 1.5 mg/L or less, such as 1.0 mg/L or less, such as 0.75 mg/L or less, such as 0.6 mg/L or less, such as 0.3 mg/L or less, such as 0.25 mg/L or less, such as 0.15 mg/L or less, such as 0.1 mg/L or less and including 0.05 mg/L or less.

Aspects of the present disclosure also include methods for in vivo monitoring analyte levels over time with analyte sensors incorporating an enzyme composition containing nicotinamide adenine dinucleotide phosphate (NAD(P)+) or derivative thereof, NAD(P)+-dependent dehydrogenase, NAD(P)H oxidoreductase and electron transfer agent. Generally, in vivo monitoring the concentration of analyte in a fluid of the body of a subject includes inserting at least partially under a skin surface an in vivo analyte sensor as disclosed herein, contacting the monitored fluid (interstitial, blood, dermal, and the like) with the inserted sensor, and generating a sensor signal at the working electrode. The presence and/or concentration of analyte detected by the analyte sensor may be displayed, stored, forwarded, and/or otherwise processed. A variety of approaches may be employed to determine the concentration of analyte (e.g., glucose, an alcohol, a ketone, lactate, β-hydroxybutyrate) with the subject sensors. In certain aspects, an electrochemical analyte concentration monitoring approach is used. For example, monitoring the concentration of analyte using the sensor signal may be performed by coulometric, amperometric, voltammetric, potentiometric, or any other convenient electrochemical detection technique.

These methods may also be used in connection with a device that is used to detect and/or measure another analyte, including glucose, oxygen, carbon dioxide, electrolytes, or other moieties of interest, for example, or any combination thereof, found in a bodily fluid, including subcutaneous e.g., interstitial fluid, dermal fluid, blood or other bodily fluid of interest or any combination thereof In certain embodiments, the method further includes attaching an electronics unit to the skin of the patient, coupling conductive contacts of the electronics unit to contacts of the sensor, collecting data using the electronics unit regarding a level of analyte from signals generated by the sensor, and forwarding the collected data from electronics unit to a receiver unit, e.g., by RF. The receiver unit may be a mobile telephone. The mobile telephone may include an application related to the monitored analyte. In certain embodiments, analyte information is forwarded by RFID protocol, Bluetooth, and the like.

The analyte sensor may be positionable in a user for automatic analyte sensing, either continuously or periodically. Embodiments may include monitoring the level of the analyte over a time period which may range from seconds, minutes, hours, days, weeks, to months, or longer. Future analyte levels may be predicted based on information obtained, e.g., the current lactate level at time zero as well as an analyte rate of change.

The sensor electronics unit may automatically forward data from the sensor/electronics unit to one or more receiver units. The sensor data may be communicated automatically and periodically, such as at a certain frequency as data is obtained or after a certain time period of sensor data stored in memory. For example, sensor electronics coupled to an in vivo positioned sensor may collect the sensor data for a predetermined period of time and transmit the collected data periodically (e.g., every minute, five minutes, or other predetermined period) to a monitoring device that is positioned in range from the sensor electronics.

In other embodiments, the sensor electronics coupled to the in vivo positioned sensor may communicate with the receiving device non automatically manner and not set to any specific schedule. For example, the sensor data may be communicated from the sensor electronics to the receiving device using RFID technology, and communicated whenever the sensor electronics are brought into communication range of the analyte monitoring device. For example, the in vivo positioned sensor may collect sensor data in memory until the monitoring device (e.g., receiver unit) is brought into communication range of the sensor electronics unit—e.g., by the patient or user. When the in vivo positioned sensor is detected by the monitoring device, the device establishes communication with the analyte sensor electronics and uploads the sensor data that has been collected since the last transfer of sensor data, for instance. In this way, the patient does not have to maintain close proximity to the receiving device at all times, and instead, can upload sensor data when desired by bringing the receiving device into range of the analyte sensor. In yet other embodiments, a combination of automatic and non-automatic transfers of sensor data may be implemented in certain embodiments. For example, transfers of sensor data may be initiated when brought into communication range, and then continued on an automatic basis if continued to remain in communication range.

EXPERIMENTAL

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Experiments were performed to demonstrate the performance of analyte sensors having a working electrode that contains nicotinamide adenine dinucleotide phosphate (NAD(P)*) or derivative thereof, NAD(P)*-dependent dehydrogenase, NAD(P)H oxidoreductase and electron transfer agent. The sensors were prepared by depositing onto the surface of an electrode an enzyme composition containing nicotinamide adenine dinucleotide phosphate, D-3-hydroxybutyrate dehydrogenase, diaphorase and a polymer bound osmium-transition metal catalyst and a difunctional crosslinker, as shown by the scheme (also referred to as a polymeric redox mediator in further examples):

HBDH + NAD + Diaphorase

Enzyme + Coenzyme

+

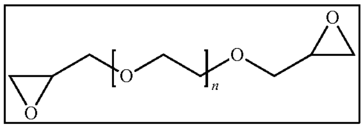

Cross-linker

+

-continued

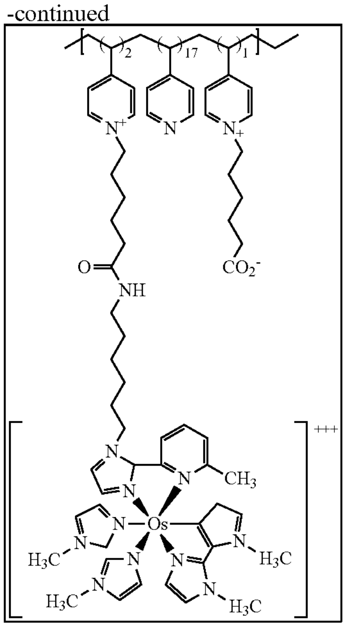

The sensors were tested in phosphate buffer containing varying concentrations of D-3-hydroxybuty rate. Table 1 summarizes beaker calibration and linearity of data signal from the prepared sensors.

TABLE 1

| | D-3-Hydroxybutyrate Sensor |
|---|---|
| Slope | 0.0163 |
| $R^2$ | 0.9982 |

Figure 2:
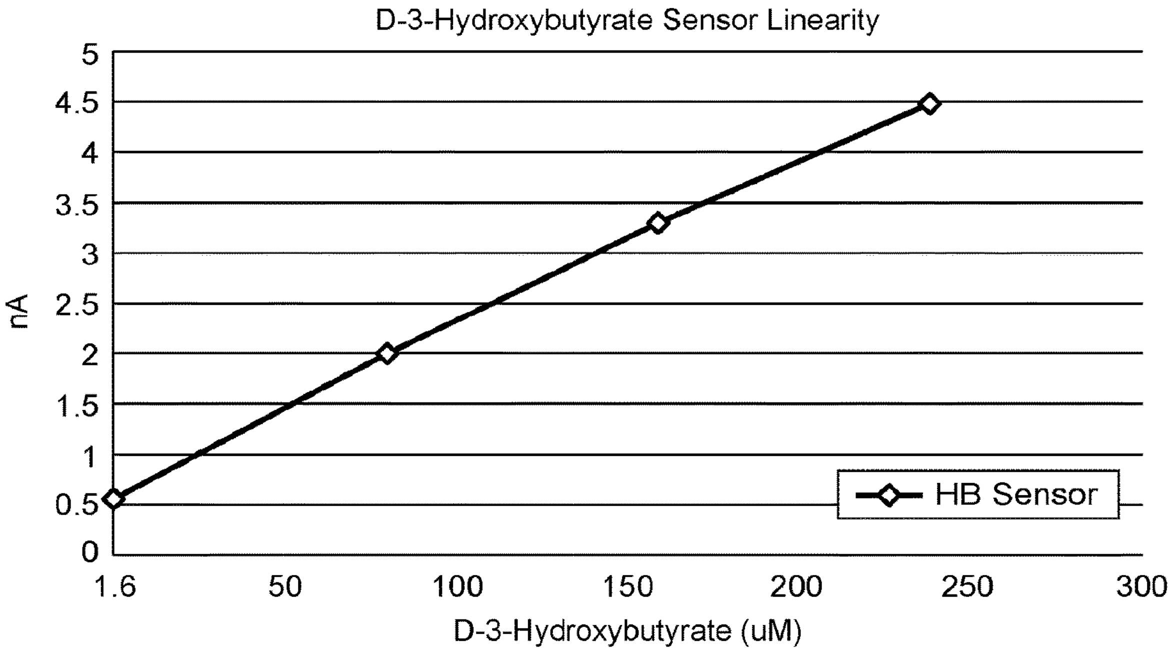
FIG. 2 depicts the linearity of the sensor signal of a D-3-hydroxybutyrate dehydrogenase sensor as a function of D-3-hydroxybutyrate concentration.

FIG. 1 shows the signal output over the course of 2.3 hours at varying concentrations of D-3-hydroxybutyrate (80 μM, 160 μM and 240 μM). FIG. 2 depicts the linearity of the sensor signal as a function of D-3-hydroxybutyrate concentration. As shown in FIGS. 1 and 2, the sensor gives a linear and persistent response to D-3-hydroxybutyrate.

Example 2

Experiments were performed to demonstrate the performance of analyte sensors having a working electrode that contains free NAD. The sensor was prepared by depositing onto the surface of an electrode an enzyme composition containing the free NAD. Sensing layer formulation is described in Table 2. The sensing layer solutions was deposit on carbon electrodes, and cured at 25 C/60H overnight, prior to addition of membrane. The membrane formulation is provided in Table 3. The sensor was dipped from above solution 3×5 mm/see, and the sensor was cured at 25 C/60H overnight, 56 C for two days.

TABLE 2

Formulation Table
Sensing Layer Solution

| BD161212 10 mM Hepes | Vendor | Cat | mg/mL | Mixing uL | Final mg/mL |
|---|---|---|---|---|---|
| D-3-Hydroxybutyrate Dehydrogenase (HBD) | Toyobo | HBD-301 | 40 | 20 | 8.89 |
| Diaphorase | Toyobo | DAD-311 | 40 | 20 | 8.89 |
| NAD | Sigma | N0632 | 20 | 10 | 2.22 |
| Polymeric redox mediator | | | 40 | 20 | 8.89 |
| Peg400 | | | 40 | 20 | 8.89 |
| Total | | | | 90 | |

TABLE 3

Membrane Coating
Membrane Solution

| Solution A | Vendor | Cat | MW | Mixing |
|---|---|---|---|---|
| Poly(4-vinylpyridine) | Sigma | 472352 | 106K | 120 mg |
| Ethanol/Hepes (10 mM pH 8.0) | | | | 1 mL |
| **Solution B** | **Vendor** | **Cat** | | **Mixing** |
| Poly(ethylene glycol) diglycidyl ether (PEGDGE 400) | Polysciences | 8210 | | 100 mg |
| Ethanol/Hepes (10 mM pH 8.0) | | | | 1 mL |
| **Final membrane solution** | | | | **Mixing (mL)** |
| Solution A | | | | 4 |
| Solution B | | | | 0.4 |

Figure 3:
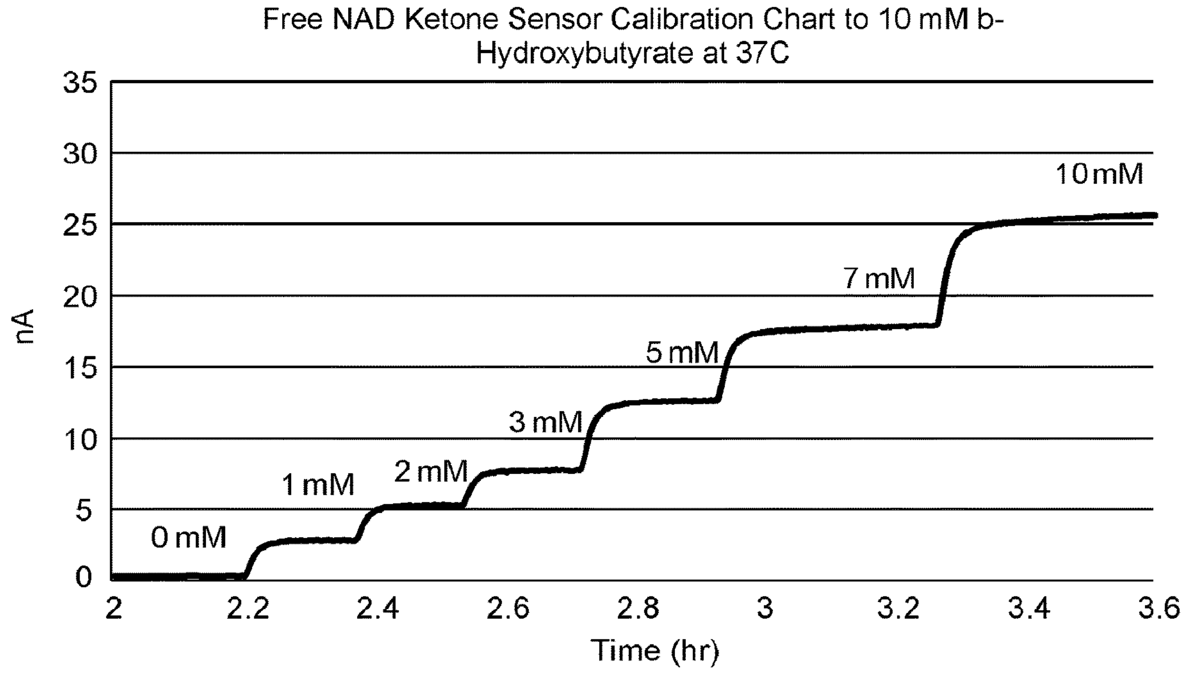
FIG. 3 shows the signal output for a D-3-hydroxybutyrate dehydrogenase sensor using free NAD over the course of 3.6 hours at varying concentrations of D-3-hydroxybutyrate according to certain embodiments.
Figure 4:
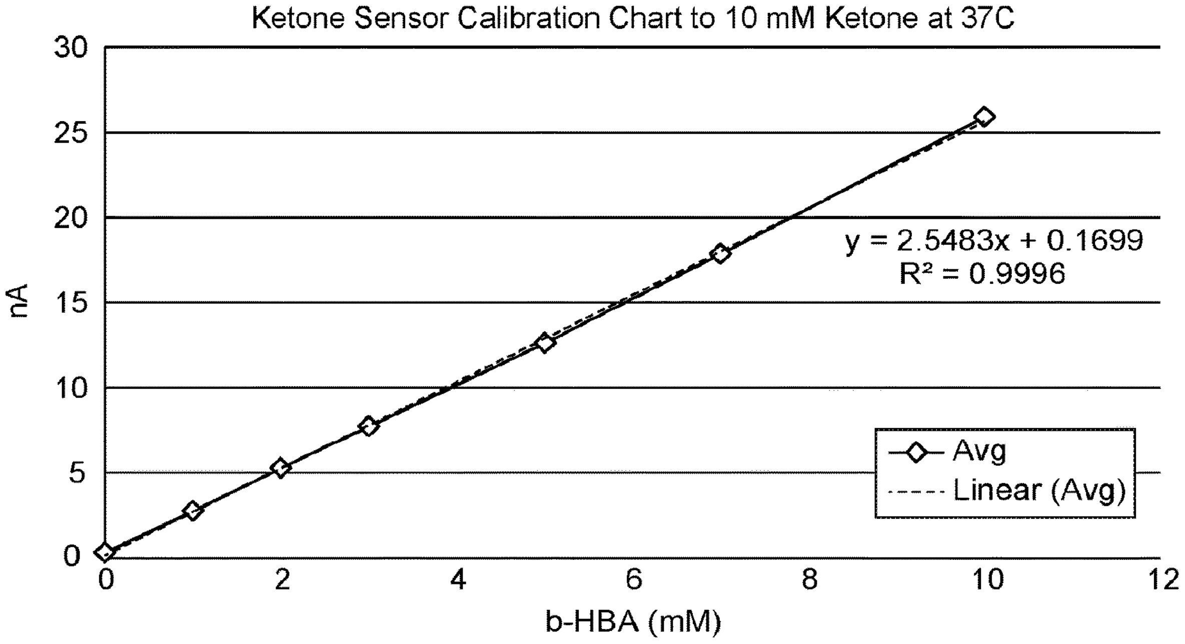
FIG. 4 depicts the linearity of the sensor signal of a D-3-hydroxybutyrate dehydrogenase sensor as a function of D-3-hydroxybutyrate concentration (Ketone).
Figure 5:
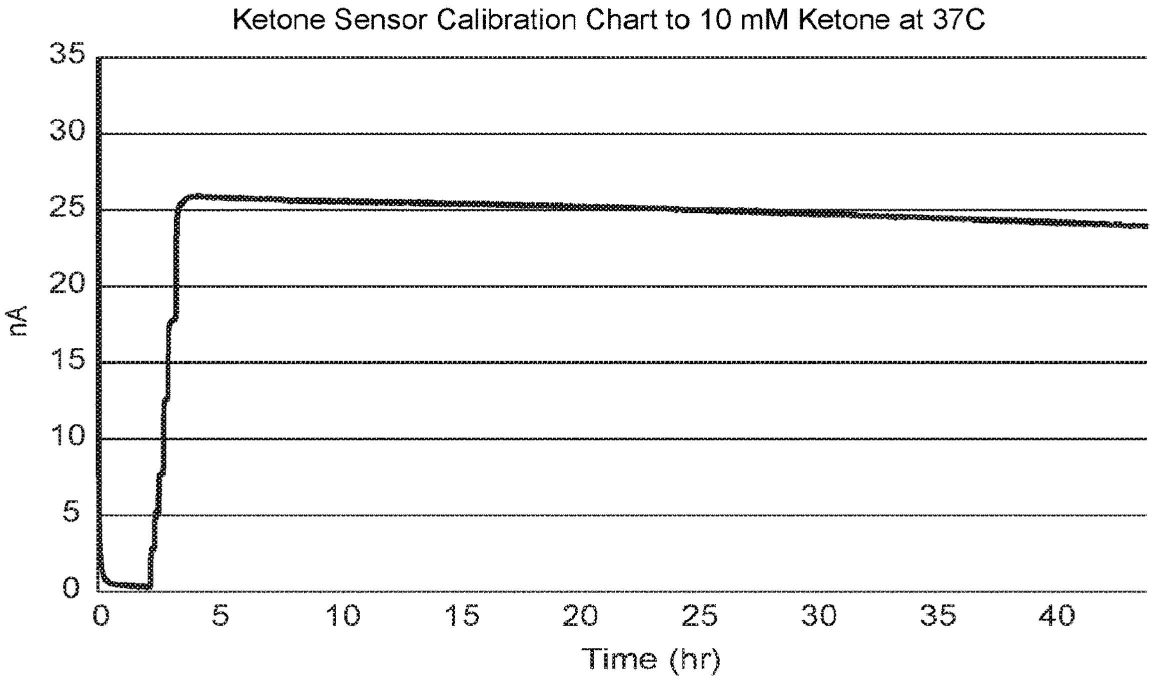
FIG. 5 depicts the stability of the sensor signal of a D-3-hydroxybutyrate dehydrogenase sensor.

FIG. 3 shows the signal output over the course of 3.6 hours at varying concentrations of D-3-hydroxybutyrate (ketone). FIG. 4 depicts the linearity of the sensor signal as a function of D-3-hydroxybutyrate concentration. FIG. 5 shows sensor calibration at 10 mM. As shown in FIGS. 3-5, the sensor gives a linear and persistent response to D-3-hydroxybutyrate (ketone). Table 4 also shows the free NAD Ketone Sensor Beaker Calibration and Stability Summary. TABLE 4

TABLE 4

| | |
|---|---|
| Slope | 2.55 |
| $R^2$ | 0.9996 |
| Decay in 45 hours | −8% |

Example 3

Figure 6:
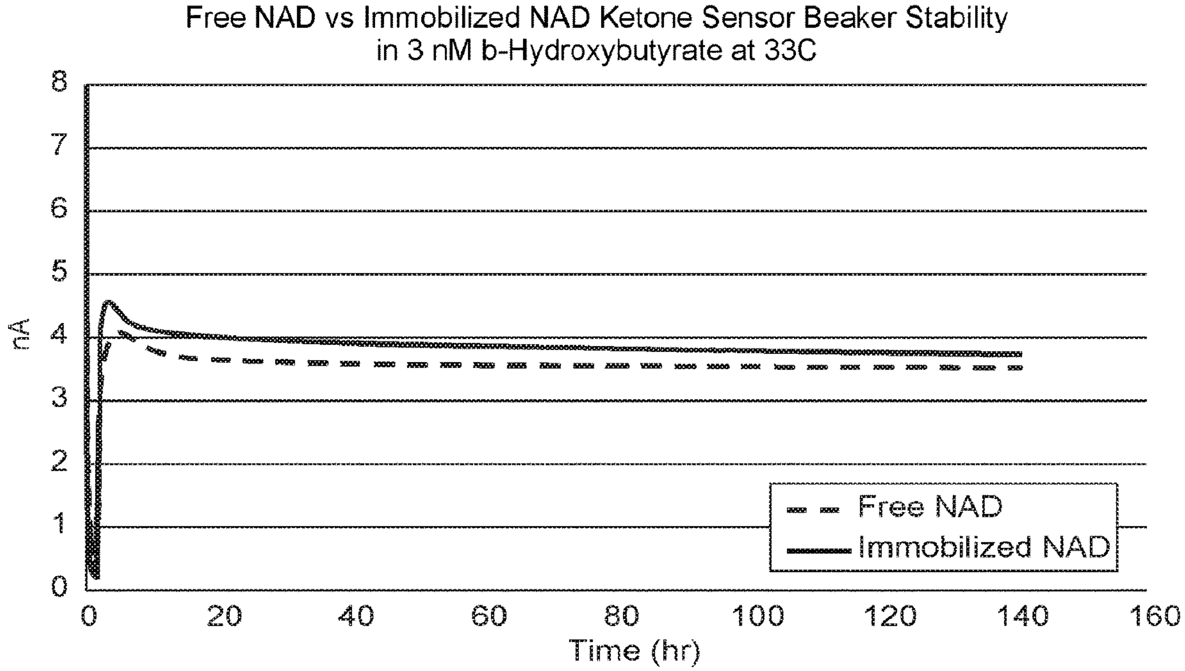
FIG. 6 depicts the stability of the sensor signal of a free NAD and immobilized NAD sensor.

Experiments were also performed to demonstrate the performance of ketone sensors having a working electrode that contains free NAD versus immobilized NAD. The sensors were prepared by depositing onto the surface of an electrode an enzyme composition containing the free NAD (A) or the immobilized NAD (B). Sensing layer formulation is described in Table 5. The sensing layer solutions was deposit on carbon electrodes, and cured at 25 C/60H overnight, prior to addition of membrane. The membrane formulation is provided in Table 6. The sensor was dipped (Table 7) from above solution 3×5 mm/see, and the sensor was cured at 25 C/60H overnight, 56 C for two days. FIG. 6 shows that both the free and immobilized NAD versions of the ketone sensor show similar stabilities and signals.

TABLE 5

| Sensing Layer Solution | | | | | | | |
|---|---|---|---|---|---|---|---|
| BD161116 | | | mg/ | Mixing uL | | Final Mg/mL | |
| 10 mM Hepes | Vendor | Cat | mL | A | B | A | B |
| D-3-Hydroxybutyrate Dehydrogenase (HBD) | Toyobo | HBD-301 | 40 | 20 | 20 | 8.89 | 8.89 |
| Diaphorase | Toyobo | DAD-311 | 40 | 20 | 20 | 8.89 | 8.89 |
| NAD | Sigma | N0632 | 20 | 10 | | 2.22 | 0.00 |
| NAD-NH2 | Biotium | | 40 | | 10 | 0.00 | 4.44 |
| Glutaraldehyde | | | 10 | 0 | 5 | 0.00 | 0.56 |
| Polymeric redox mediator | | | 40 | 20 | 20 | 8.89 | 8.89 |
| Peg400 | | | 40 | 20 | 20 | 8.89 | 8.89 |
| Total | | | | 90 | 95 | | |

TABLE 6

| Membrane Coating Membrane Solution | | | |
|---|---|---|---|
| Solution A | Vendor | MW | Mixing |
| Smart Membrane | ADC | 160K | 120 mg |
| Ethanol/Hepes (10 mM pH 8.0) | | | 1 mL |
| Solution B | Vendor | Cat | Mixing |
| Poly(ethylene glycol) diglycidyl ether (PEGDGE 400) | Polysciences | 8210 | 100 mg |
| Ethanol/Hepes (10 mM pH 8.0) | | | 1 mL |
| Final membrane solution | Mixing (mL) | | |
| Solution A | 4 | | |
| Solution B | 0.35 | | |

TABLE 7

| Membrane Dipping Condition (Free NAD sensor was coated thicker membrane than Immobilized NAD sensor) | |
|---|---|
| SL Solution | Dipping |
| A (Free NAD) | 4 × 5 |
| B (Immobilized NAD) | 3 × 5 |

What is claimed is:

1. An electrochemical analyte sensor comprising a first portion configured to be positioned above a user's skin and a second portion configured to be transcutaneously positioned in the user's skin and in contact with the user's biological fluid to monitor the level of an analyte in vivo, the second portion comprising:
   i) an electrode;
   ii) an enzyme composition disposed upon the electrode, the enzyme composition comprising:
      a) nicotinamide adenine dinucleotide (phosphate) (NAD(P)+) or derivative thereof;
      b) D-3-hydroxybutyrate dehydrogenase;
      c) diaphorase;
      d) a polymeric redox mediator, and
   iii) a membrane disposed on the enzyme composition,
   wherein at least one of the D-3-hydroxybutyrate dehydrogenase and the diaphorase is covalently bonded to the polymeric redox mediator, and
   wherein the NAD(P)+ or derivative thereof is not covalently bonded to the polymeric redox mediator.

2. The analyte sensor of claim 1, wherein the D-3-hydroxybutyrate dehydrogenase is covalently bonded to the polymeric redox mediator.

3. The analyte sensor of claim 1, wherein the diaphorase is covalently bonded to the polymeric redox mediator.

4. The analyte sensor of claim 1, wherein the D-3-hydroxybutyrate dehydrogenase and the diaphorase are covalently bonded to the polymeric redox mediator.

5. The analyte sensor of claim 1, wherein the enzyme composition comprises NAD(P)+.

6. The analyte sensor of claim 1, wherein the composition comprises a derivative of NAD(P)+.

7. The analyte sensor of claim 5, wherein the polymeric redox mediator comprises a heterocycle-containing polymer and the enzyme composition further comprises a crosslinker.

8. The analyte sensor of claim 5, wherein the polymeric redox mediator comprises a transition metal complex.

9. The analyte sensor of claim 8, wherein the transition metal complex is an osmium complex with one or more ligands, wherein each ligand comprises a nitrogen-containing heterocycle.

10. The analyte sensor of claim 9, wherein the one or more ligands comprise three heterocyclic nitrogen-containing bidentate ligands.

11. The analyte sensor of claim 9, wherein the one or more ligands comprise two biimidazole and one imidazole-pyridine bidentate ligands.

12. The analyte sensor of claim 7, wherein the heterocycle-containing polymer comprises polyvinylpyridine.

13. The analyte sensor of claim 7, wherein the crosslinker is a polyethylene glycol (PEG) multi-arm epoxide.

14. The analyte sensor of claim 7, wherein the polymeric redox mediator comprises polyvinylpyridine and the crosslinker is a polyethylene (PEG) multi-arm epoxide.

15. The analyte sensor of claim 5, wherein the membrane comprises polyurethane or polyether urethane.

16. The analyte sensor of claim 5, wherein the membrane comprises a crosslinked polyvinylpyridine or polyvinylimidazole.

17. The analyte sensor of claim 16, wherein the membrane further comprises poly(ethylene glycol).

18. The analyte sensor of claim 14, wherein the membrane comprises polyurethane or polyether urethane.

19. The analyte sensor of claim 14, wherein the membrane comprises a crosslinked polyvinylpyridine or polyvinylimidazole.

20. The analyte sensor of claim 19, wherein the membrane further comprises poly(ethylene glycol).

21. An electrochemical analyte sensor comprising a first portion configured to be positioned above a user's skin and a second portion configured to be transcutaneously positioned in the user's skin and in contact with the user's biological fluid to monitor the level of ketones in vivo, the second portion comprising:
   i) an electrode;
   ii) an enzyme composition disposed upon the electrode, the enzyme composition comprising:
      a) nicotinamide adenine dinucleotide (phosphate) (NAD(P)+) or derivative thereof,
      b) D-3-hydroxybutyrate dehydrogenase;
      c) diaphorase;
      d) an electron transfer agent; and
      e) a polymer; and iii) a membrane disposed on the enzyme composition, wherein at least one of the D-3-hydroxybutyrate dehydrogenase and the diaphorase is covalently bonded to the polymer, and wherein the NAD(P)+ or derivative thereof is not covalently bonded to the polymer.

22. The analyte sensor of claim 21, wherein the D-3-hydroxybutyrate dehydrogenase is covalently bonded to the polymer.

23. The analyte sensor of claim 21, wherein the diaphorase is covalently bonded to the polymer.

24. The analyte sensor of claim 21, wherein the D-3-hydroxybutyrate dehydrogenase and the diaphorase are covalently bonded to the polymer.

25. The analyte sensor of claim 24, wherein the enzyme composition comprises NAD(P)+.

26. The analyte sensor of claim 25, wherein the polymer is a heterocycle-containing polymer.

27. The analyte sensor of claim 26, wherein the heterocycle-containing polymer comprises polyvinylpyridine.

28. The analyte sensor of claim 26, wherein the heterocycle-containing polymer is crosslinked with a polyethylene glycol (PEG) multi-arm epoxide.

29. The analyte sensor of claim 26, wherein the electron transfer agent comprises a transition metal complex.

30. The analyte sensor of claim 29, wherein the transition metal complex is covalently bonded to the polymer.

31. The analyte sensor of claim 29, wherein the transition metal complex is an osmium complex with one or more ligands, wherein each ligand comprises a nitrogen-containing heterocycle.

32. The analyte sensor of claim 25, wherein the membrane comprises polyurethane or polyether urethane.

33. The analyte sensor of claim 25, wherein the membrane comprises a crosslinked polyvinylpyridine or polyvinylimidazole.

34. The analyte sensor of claim 33, wherein the membrane further comprises poly(ethylene glycol).

35. The analyte sensor of claim 27, wherein the membrane comprises polyurethane or polyether urethane.

36. The analyte sensor of claim 27, wherein the membrane comprises a crosslinked polyvinylpyridine or polyvinylimidazole.

37. The analyte sensor of claim 36, wherein the membrane further comprises poly(ethylene glycol).

* * * * *